US00PP28947P2

(12) United States Plant Patent
van Langen

(10) Patent No.: US PP28,947 P2
(45) Date of Patent: Feb. 6, 2018

(54) ***ALOE* PLANT NAMED 'AMIAL1619'**

(50) Latin Name: *Aloe aristata*
Varietal Denomination: AMIAL1619

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/530,589

(22) Filed: Feb. 3, 2017

(51) Int. Cl.
*A01H 5/12* (2006.01)

(52) U.S. Cl.
USPC ..... Plt./373

(58) Field of Classification Search
USPC ..... Plt./373, 372
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Aloe aristata* cultivar named 'AMIAL1619' which is characterized by erect foliage that is arranged in a spreading basal rosette, with foliage in the innermost whorls held very tightly. The large deltoid foliage exhibits a soft mucronulate apex, dark green general coloration, and is densely covered with prominent papillae, many of which bear spines. Papillae on the abaxial leaf surface are arranged in distinct transverse rows. The new variety has shown to be uniform and stable in the resulting generations from asexual propagation.

4 Drawing Sheets

Latin name of the genus and species: The Latin name of the genus and species of the novel variety disclosed herein is *Aloe aristata.*

Variety denomination: The inventive variety of *Aloe* disclosed herein has been given the variety denomination 'AMIAL1619'.

BACKGROUND OF THE INVENTION

Parentage: 'AMIAL1619' originated as a naturally occurring, whole-plant mutation of The species *Aloe aristata* (not a named variety or cultivar unpatented). In Spring of 2016 The inventor discovered the mutation at a commercial greenhouse in Heerhugowaard, the Netherlands, growing amongst a crop of the species *Aloe aristata*. The mutation was noted for its erect foliage and prominent white papillae and was subsequently isolated for further evaluation in order to confirm the distinctness and stability of the characteristics first observed. Upon confirmation of distinctness and stability, 'AMIAL1619' was selected for commercialization in the summer of 2016.

Asexual Reproduction: Asexual reproduction of the new cultivar 'AMIAL1619', by way of rooting leaf cuttings, was first initiated in the summer of 2016 at the inventor's commercial greenhouse in Heerhugowaard, The Netherlands. The claimed plant has since been asexually propagated by way of meristematic tissue culture propagation. Through two subsequent generations, the unique features of this cultivar have proven to be stable and true to type.

SUMMARY OF THE INVENTION

The cultivar 'AMIAL1619' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1619'. These characteristics in combination distinguish 'AMIAL1619' as a new and distinct *Aloe aristata* cultivar:

1. 'AMIAL1619' exhibits erect to slightly inward-facing foliage arranged in a spreading basal rosette, with foliage in the innermost whorls held very tightly; and
2. 'AMIAL1619' exhibits large deltoid leaves with a soft mucronulate apex; and
3. 'AMIAL1619' exhibits dark green foliage that is densely covered with prominent papillae on both the adaxial and abaxial surfaces; and
4. 'AMIAL1619' exhibits papillae near the margins and apex which bear spines; and
5. 'AMIAL1619' exhibits papillae on the abaxial leaf surface which are arranged in distinct transverse rows, and bearing spines in a distinct longitudinal row along the midrib.

BOTANICAL DESCRIPTION OF THE PLANT

Figure 1:
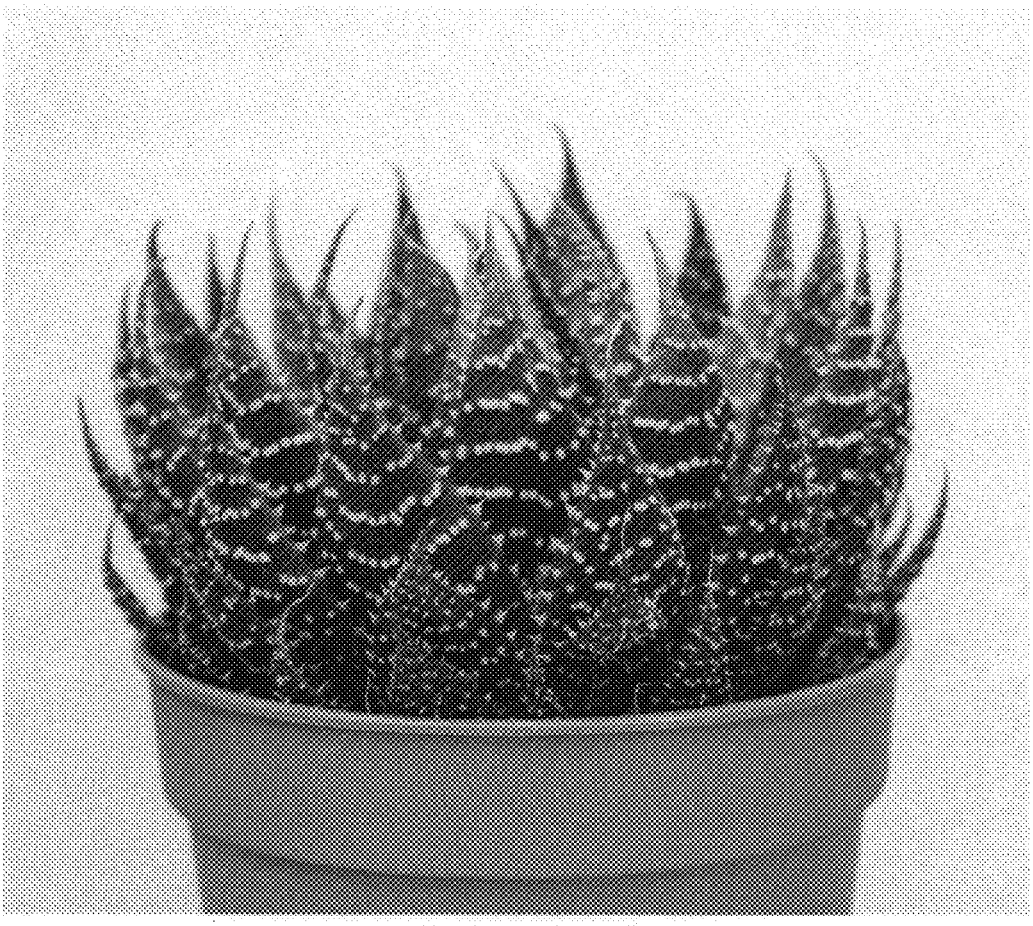
FIG. 1 illustrates, as nearly true as it is reasonably possible to make the same in color photographs of this type, an exemplary plant of 'AMIAL1619' grown in a commercial greenhouse in Heerhugowaard, The Netherlands. This plant is approximately 9 months old, shown planted in a 10.5 cm container.
Figure 2:
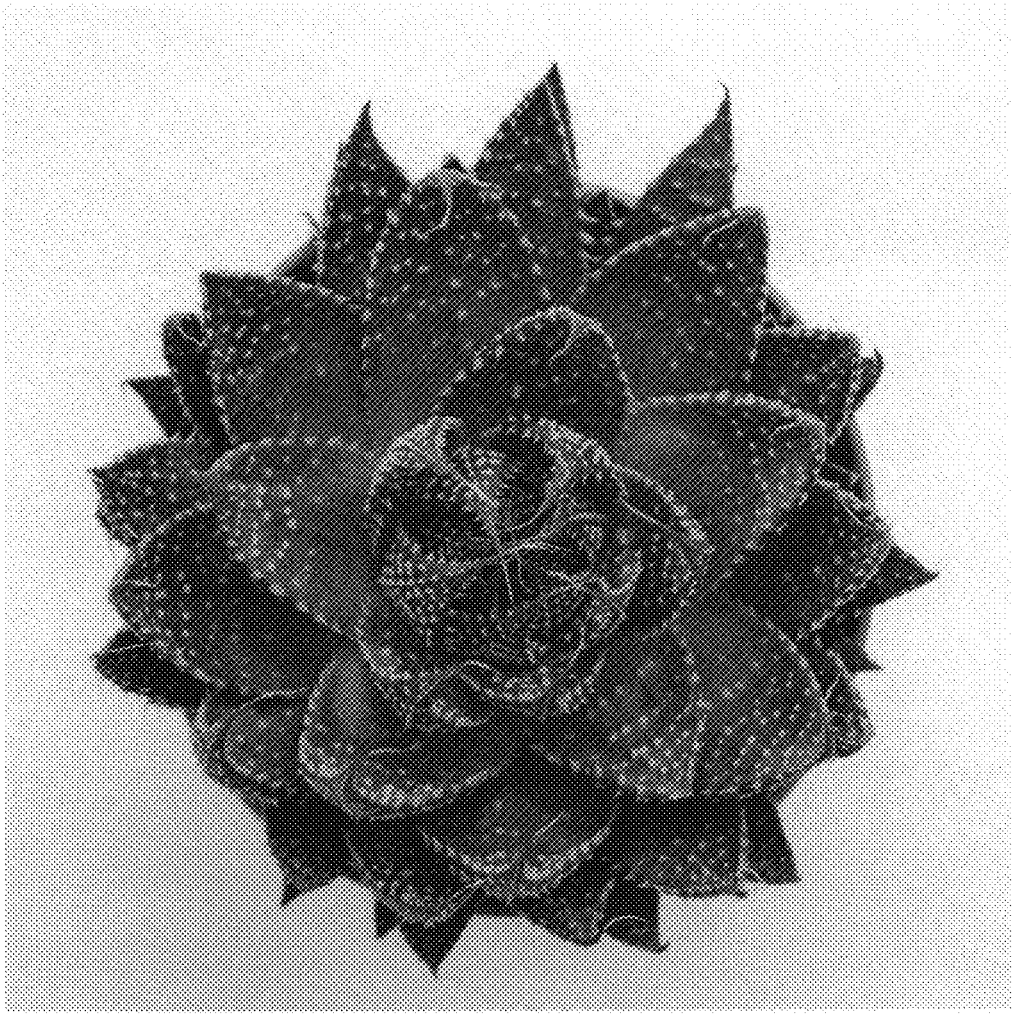
FIG. 2 illustrates, as nearly true as it is reasonably possible to make the same in color photographs of this type, the typical foliage arrangement of 'AMIAL1619.
Figure 3:
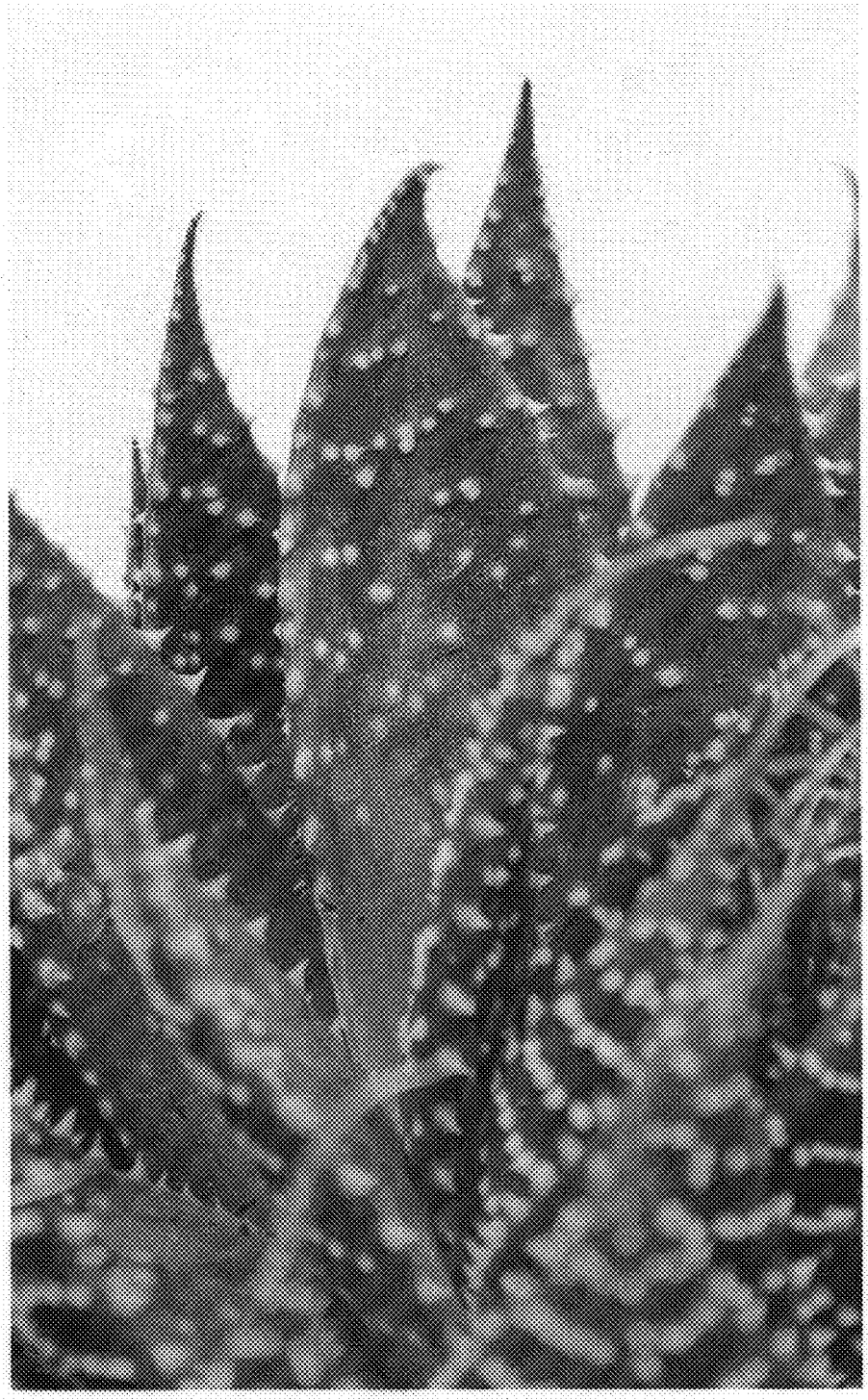
FIG. 3 illustrates, as nearly true as it is reasonably possible to make the same in color photographs of this type, the adaxial surface of the mature foliage 'AMIAL1619'.
Figure 4:
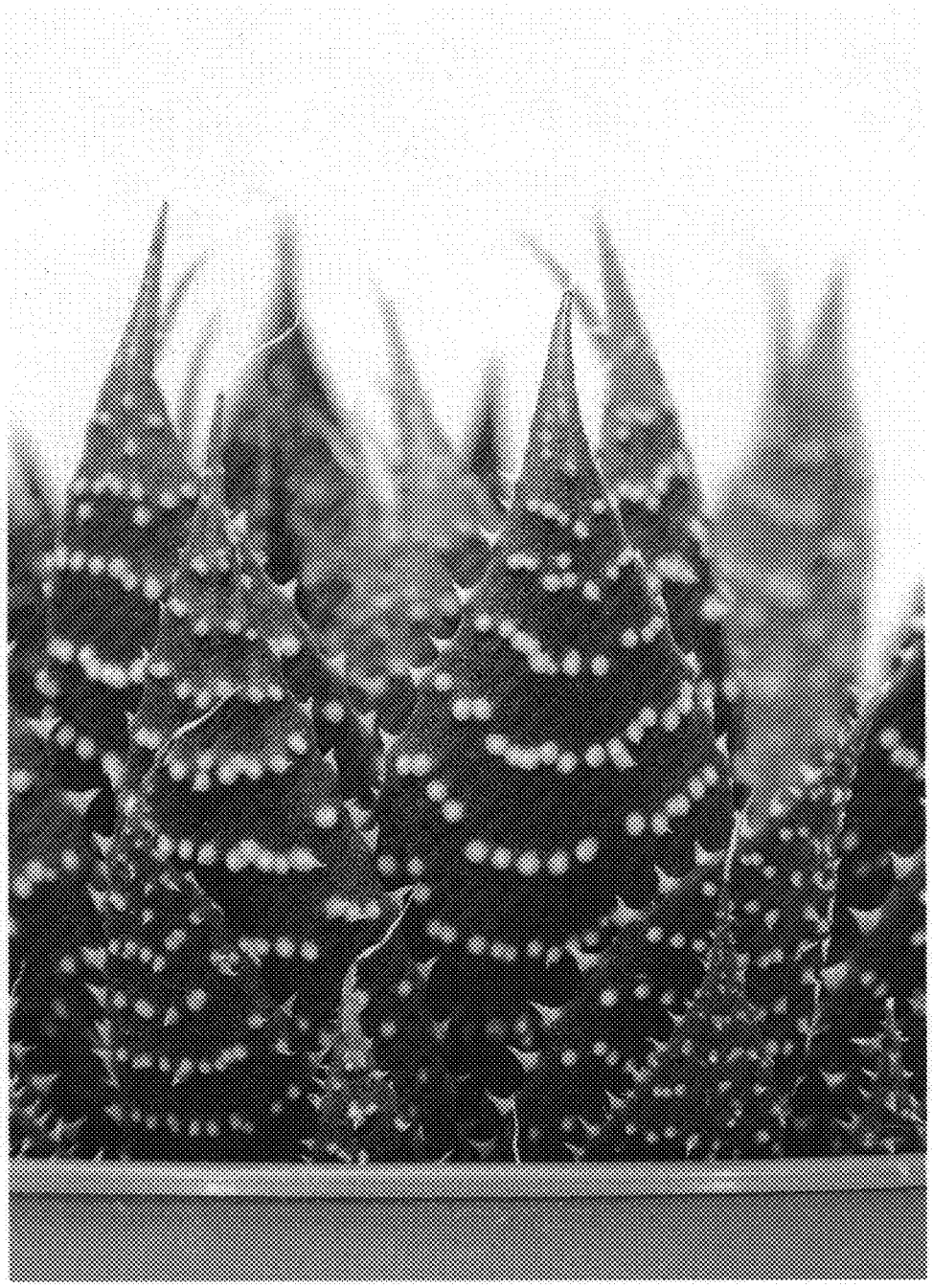
FIG. 4 illustrates, as nearly true as it is reasonably possible to make the same in color photographs of this type, the abaxial surface of the mature foliage 'AMIAL1619'.

The following observations and measurements made in January of 2017 describe averages from a sample set of six specimens of 9 months old 'AMIAL1619' plants grown in 11 cm nursery containers at commercial greenhouse in Heerhugowaard, The Netherlands. Plants were produced using conventional greenhouse production protocols for *Aloe* which consisted of minimal irrigation and fertilizer applications, and chemical pest and disease control measures against mealy bug, *Botrytis* and *Fusarium* as required. Plants were grown under approximately 50 percent shade and no photoperiodic treatments or artificial light was given to the plants.

Those skilled in the art will appreciate that certain characteristics will vary with older or, conversely, with younger plants. 'AMIAL1619' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1619' and a comparison with the parent and closest known comparator an unnamed, unpatented plant of, *Aloe aristata*, is provided below.

Plant description:

*Growth habit*.—Succulent perennial with foliage growing in a non-branched basal rosette.

*Plant shape*.—Globular.

*Height from soil level to top of foliar plane*.—9.7 cm.

*Plant spread*.—Average of 14.0 cm.

*Growth rate*.—Moderate.

*Plant vigor*.—Moderate.

*Propagation*.—Type — Leaf cuttings and meristematic tissue culture. Time to initiate rooting — Approximately 25 days at 18 degrees Celsius. Crop time — Approximately 18 to 22 weeks to produce a marketable plant in a 7 cm container.

*Disease and pest resistance or susceptibility*.—Neither resistance nor susceptibility to typical *Aloe aristata* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 66 leaves per rosette.

*Shape*.—Thick, succulent leaves which are oblong to narrow deltoid.

*Dimensions*.—9.3 cm long, 3.2 cm wide, and 1.0 cm thick, on average.

*Aspect*.—Slightly concaved.

*Attitude*.—Very erect to slightly inward facing at the inner whorls.

*Apex*.—Narrow apiculate with a soft mucronulate tip.

*Base*.—Broad cuneate.

*Margin*.—Dentate; not undulated or lobed.

*Texture, adaxial surface*.—Glabrous and moderately covered with large orbicular papillae, each approximately 1.0 mm high and 1.0 mm in diameter; papilla bearing spines near margins and apex.

*Texture, abaxial surface*.—Glabrous and densely covered with prominent papillae, more or less arranged in axial rows; each papilla approximately 1.0 mm high and 1.0 mm in diameter; papilla bearing spines near margins, apex, and in a distinct longitudinal row along the midrib.

*Luster, adaxial surface*.—Slightly to moderately glossy.

*Luster, abaxial surface*.—Slightly glossy.

*Color*.—Juvenile foliage, adaxial surface — Green, nearest to RHS NN137D, and fading to yellow-green towards the base, nearest to RHS 146D; papillae are greyed-green, nearest to RHS 192D. Juvenile foliage, abaxial surface — Green, nearest to RHS NN137C, and fading to yellow-green towards the base, nearest to RHS 145A; papillae are colored in between green-white, RHS 157D, and greyed-green, RHS 191D. Mature foliage, adaxial surface — In between green, RHS NN137A, and yellow-green, slightly darker than RHS 147A; fading lighter towards the base, nearest to a combination of RHS 147B, 147C, and 147D; papillae are greyed-green, RHS 192D. Mature foliage, abaxial surface — In between green, RHS NN137A, and yellow-green, RHS 147A; fading lighter towards the base, nearest to a combination of RHS 147B, 147C, and 147D; papillae are colored in between green-white, RHS 157D, and greyed-green, RHS 191D.

*Venation*.—No venation is visible.

*Petiole*.—No petiole; leaves are sessile.

Inflorescence: No flowering has been observed to date.

Comparisons With the Parent Plant and Closest Known Comparator

Plants of the new cultivar 'AMIAL1619' differ from the parent, *Aloe aristata*, which is also the closest known comparator, in the following characteristics described in Table 1 below.

TABLE 1

| Characteristic | 'AMIAL1619' | Unnamed plant of *Aloe aristata* |
|---|---|---|
| Leaf size. | Leaves are larger than those of the parent; broader and longer. | Leaves are smaller. |
| General coloration of mature foliage. | Dark green. | Green to yellow green and suffused with greyed-green. |
| Leaf papillae. | Prominent papilla that are white in color; arranged in rows on the abaxial leaf surface. Papilla bearing spines near margins, apex, and in a distinct longitudinal row along the midrib of the abaxial surface. | Papillae are smaller, less prominent, green-white in color, and occur randomly on the abaxial surface; none of the papilla bearing spines. |
| Leaf attitude. | Very erect to slightly inward-facing. | Erect to slightly outward facing. |

That which is claimed is:

1. A new and distinct variety of *Aloe aristata* plant named 'AMIAL1619', substantially as described and illustrated herein.

* * * * *